US008977727B2

(12) United States Patent
Birtwhistle (10) Patent No.: US 8,977,727 B2
(45) Date of Patent: Mar. 10, 2015

(54) REMOTE CONFIGURATION AND SELECTIVE DISTRIBUTION OF PRODUCT CONTENT TO MEDICAL DEVICES

(75) Inventor: Daniel Birtwhistle, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 101 days.

(21) Appl. No.: 13/195,975

(22) Filed: Aug. 2, 2011

(65) Prior Publication Data
US 2013/0036210 A1 Feb. 7, 2013

(51) Int. Cl.
*G06F 15/177* (2006.01)
*G06F 19/00* (2011.01)
(52) U.S. Cl.
CPC .................................. *G06F 19/3412* (2013.01)
USPC .......................................... 709/221; 709/220
(58) Field of Classification Search
USPC .................................................. 709/220, 221
See application file for complete search history.

(56) References Cited

U.S. PATENT DOCUMENTS

| 6,202,207 | B1 | 3/2001 | Donohue |
| 2003/0143991 | A1 | 7/2003 | Minear et al. |
| 2004/0243991 | A1* | 12/2004 | Gustafson et al. ............. 717/168 |
| 2005/0216718 | A1* | 9/2005 | Rao .................................... 713/1 |
| 2006/0026304 | A1 | 2/2006 | Price |
| 2006/0074463 | A1* | 4/2006 | Seeberger et al. .............. 607/60 |
| 2006/0184927 | A1 | 8/2006 | Deblaquiere et al. |
| 2007/0136098 | A1* | 6/2007 | Smythe et al. .................... 705/3 |
| 2007/0240152 | A1* | 10/2007 | Li et al. .......................... 717/174 |
| 2008/0189693 | A1* | 8/2008 | Pathak ........................... 717/168 |
| 2008/0300919 | A1 | 12/2008 | Charlton et al. |
| 2010/0125839 | A1 | 5/2010 | Gebis et al. |
| 2011/0167250 | A1* | 7/2011 | Dicks et al. ....................... 713/2 |

FOREIGN PATENT DOCUMENTS

WO WO2004/001589 12/2003

OTHER PUBLICATIONS

Code of Federal Regulations, Title 21, Chapter I "Food and Drug Administration Department of Health and Human Services Subchapter H—Medical Devices" Apr. 1, 2010.
Dexcom Seven® Plus Software, www.dexcom.com/products/dm3_software, 3 pages. 2011.

* cited by examiner

*Primary Examiner* — Wing F Chan
*Assistant Examiner* — Padma Mundur
(74) *Attorney, Agent, or Firm* — Harness, Dickey & Pierce, P.L.C.

(57) ABSTRACT

A distribution server for distributing updates for medical devices is disclosed. The distribution server can provide an update to a configuration device which configures a device to be updated. The distribution server includes a portal that allows an update provider to provide an update package including an update file and update package data relating to the update file. The update package data includes dependency data indicating a condition that must be satisfied by the configuration device or a second device so that the update file can be installed on the device to be updated. The distribution server further includes a database that is configured to store package data of a plurality of update packages and locations of update files of the plurality of update packages. The server further includes a distribution module that receives an inquiry on behalf of a medical device and provides a list of available update packages.

9 Claims, 5 Drawing Sheets

REMOTE CONFIGURATION AND SELECTIVE DISTRIBUTION OF PRODUCT CONTENT TO MEDICAL DEVICES

FIELD

The present disclosure relates to a system and method for remote configuration and selective distribution of product content to medical devices. In particular, the disclosure relates to a distribution server for receiving the product content and distributing the product content to a configuration server.

BACKGROUND

Increasingly, the healthcare industry is turning to electronic medical devices to assist patients and healthcare providers manage chronic diseases. For example, a diabetes patient may carry a blood glucose meter, an insulin pump, and/or a continuous glucose meter as part of the patient's medical treatment. Furthermore, the care provider of the patient may utilize disease management software that tracks one or more patients' data. For instance, in the context of a diabetes patient, the disease management software can be configured to synchronize with one or more of the patient's medical devices and to obtain data relating to the patient's management of diabetes. The disease management system can obtain past blood glucose readings, recent insulin dosage amounts, meal histories and any other pertinent data. This information can help a treating physician make diagnoses and treatment decisions for the patient.

The disease management software may also be utilized to configure the patient's medical device. For instance, the disease management software can be configured to change parameters relating to the structured testing of a patient. The disease management software utilizes the communication path between the medical device and device hosting the disease management software, e.g., a computer of the healthcare provider, to communicate the new parameter values to the medical device.

Previously and with respect to configuration medical devices, the reach of disease management software has been limited. Specifically, disease management software is not configured to update the medical device itself. For example, disease management software cannot be used to update the communications protocol of a medical device or to update the operating system of the medical device. Traditionally, a patient would be required to update his or her own device. As many inflicted patients are elderly or children, updating a device can be a difficult task. Furthermore, as these medical devices may become integral to the patient's treatment regimen, a physician may not want to trust a patient to properly configure their own medical devices. Thus, there is a need for a tool that allows the diabetes management software of a healthcare provider to update one or more medical devices.

The background description provided herein is for the purpose of generally presenting the context of the disclosure.

SUMMARY

In one aspect of the disclosure, a distribution system for distributing a plurality of update packages to a configuration device is disclosed. The configuration device is configured to update a plurality of patient medical devices. The distribution system includes a portal that is configured to allow an update package provider to provide a new update package. The new update package includes an update file for a device to be updated and package data corresponding to the update file. The package data includes dependency data indicating a condition that must be satisfied by the configuration device so that the update file of the new update package can be installed on the device to be updated. The distribution system further comprises a database that is configured to store package data of the plurality of update packages and locations of update files of the plurality of update packages including the package data of the new update package and a location of the update file of the new update package. The distribution system further includes a distribution module that is configured to receive an inquiry from the configuration device on behalf of a patient medical device of the plurality of patient medical devices, and to provide a list of update packages including the new update package to the configuration device based on the inquiry and the dependency data of the update packages.

In another aspect of the disclosure, a distribution system for distributing a plurality of update packages to a configuration device is disclosed. The configuration device is configured to update a plurality of patient medical devices. The system comprises a portal that is configured to allow an update package provider to provide a new update package. The new update package includes an update file for a patient medical device to be updated and package data corresponding to the update file. The package data includes dependency data indicating a condition that must be satisfied by a different patient medical device so that the update file of the new update package can be installed on the patient medical device to be updated. The system further comprises a database that is configured to store package data of the plurality of update packages and locations of update files of the plurality of update packages including the package data of the new update package and a location of the update file of the new update package. The system also includes a distribution module that is configured to receive an inquiry from the configuration device on behalf of a first patient medical device of the plurality of patient medical devices, and to provide a list of update packages including the new update package to the configuration device based on the inquiry and the dependency data of the update packages.

Further areas of applicability of the present disclosure will become apparent from the detailed description provided hereinafter. It should be understood that the detailed description and specific examples are intended for purposes of illustration only and are not intended to limit the scope of the disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

A distribution system for use in updating medical devices is herein disclosed. The distribution system allows a configuration device of a healthcare provider to update a medical device of a patient. The distribution system is configured to allow providers to upload update files and data relating to the update files to the system, and provides access to configuration devices that update the medical devices of patients with one or more of the uploaded update files. As used herein, an update file can refer to any file that contains an update for a device or an application of the device. For example, an update file can be a language update that updates a language file of the medical device, a software update that updates an application running on the medical device, a firmware update that updates the medical device, or a database update that updates the database of a medical device. The distribution system will receive dependencies relating to the update file and can further determine additional dependencies based on the dependencies relating to the update file. Dependencies can indicate a set of conditions that are required in order to successfully install the update file. For example only, with respect to a firmware update for a blood glucose meter, the update provider may indicate that the most recent software update for the configuration device used to install the update is necessary. Thus, before the configuration device can update the firmware of the blood glucose meter, the configuration device will have to be updated with the most recent software update. It is noted, that the medical device may also be configured to configure itself. Thus, the medical device may be able to connect to the distribution system and to obtain an update file, which is installed by the medical device itself.

Figure 1:
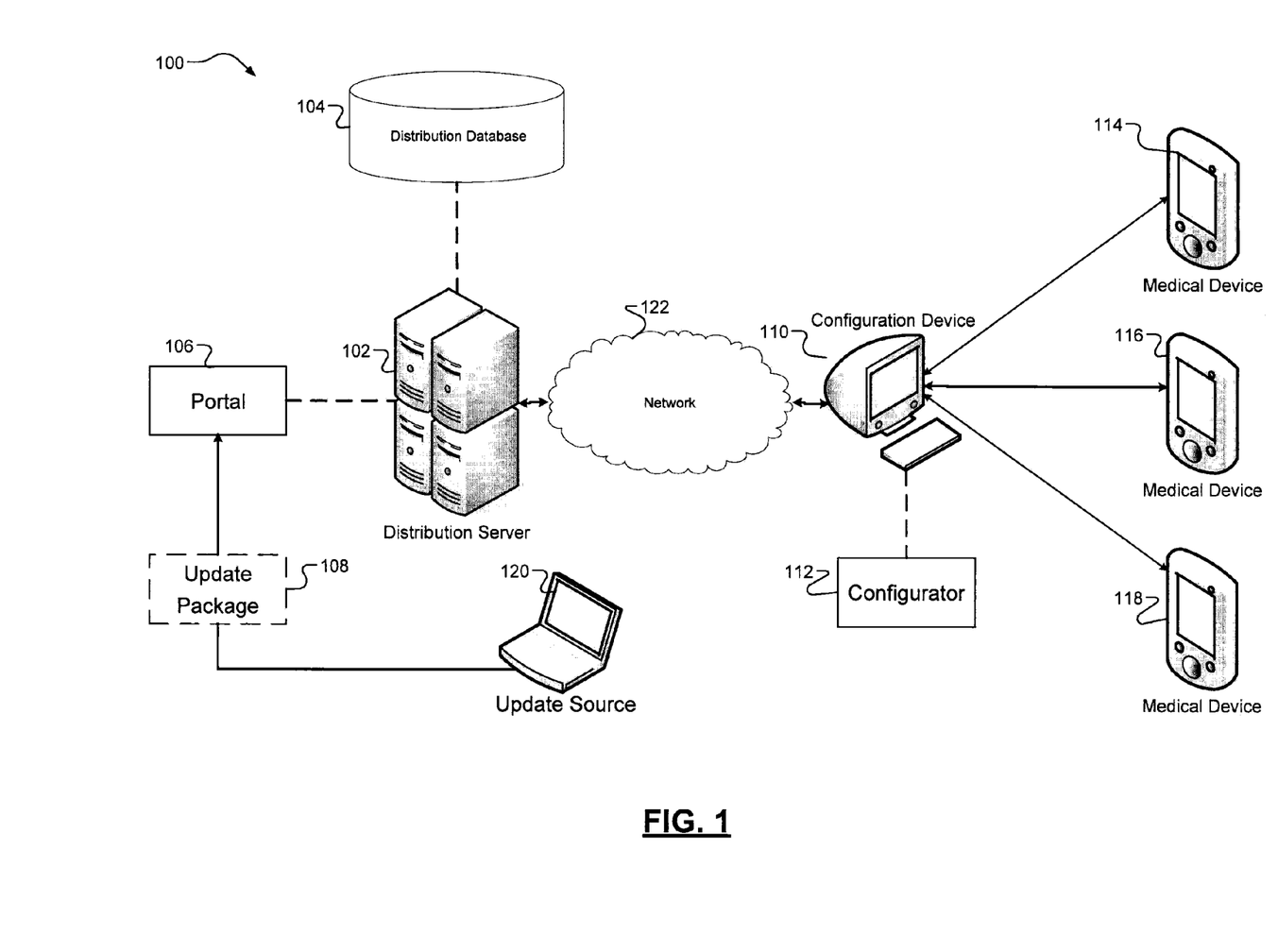
FIG. 1 is a drawing illustrating an exemplary distribution system and devices connecting thereto.

FIG. 1 illustrates an exemplary distribution system 100. The distribution system 100 includes a distribution server 102, a configuration device 110, a plurality of medical devices 114-118 and an update source 120. The distribution server 102 communicates with a configuration device 110 over a communications network 122. The configuration device 110 may include a configurator 112 that is configured to update a plurality of medical devices 114, 116, and 118 with device and application update files that are uploaded to the distribution server 102 via a portal 106. The configurator 112 may be comprised of computer executable instructions that are executed by a processor of the configuration device 110. In some embodiments, the medical device 114 is configured to obtain the update files from the distribution server 102 and configure itself. Thus, a configurator 112 may be executed by the medical device 114 as well.

A medical device 114 will connect to the configuration device 110. For example, the medical device 114 may connect to the configuration device 110 via a USB interface. Once connected to the configuration device 110, the medical device 114 will provide information relating to the device 114 to the configuration device 110. For example, the medical device 114 may store data indicating a current version of the device firmware and software, a geographic location of the medical device 114, and information relating to applications executed by the medical device 114. The configuration device 110 will use the information of the medical device 114 to generate an inquiry to the distribution server 102 requesting available updates for the medical device 114 or applications running thereon. The distribution server 102 searches a distribution database 104 using information contained in the inquiry to determine a list of available updates for the medical device 114 and/or available updates for the applications running on the medical device 114. The updates may also include updates to specific files, such as language files, or updates to a database on the medical device 114.

The distribution server 102 will provide the list of available updates to the configuration device 110. The distribution server 102 will also provide a list of dependant updates to the configuration device 110. The list of dependant updates include updates that are to be performed in order to install an update in the list of available updates. The dependant updates may be updates for the medical device 114, another medical device 116 or the configuration device 110. For example, if a firmware update is available for the medical device 114, but the configuration device 110 must be updated with a more recent firmware version, the more recent firmware version for the configuration device 110 would be a dependant update. The configuration device 110 will download one or more of the available updates and dependant updates and will install the updates on the medical device 114, another medical device 116, an application executed by the medical device 114 and/or the configuration device 110.

The distribution server 102 stores update packages in a distribution database 104. An update package 108 is provided to the distribution server 102 via the portal. The update package 108 includes an update file and update package data. An update file can be any type of update including software updates, firmware updates, middleware updates, application updates, language file updates, database updates, or the like. The update package data includes an update identifier that uniquely identifies the update file, an attribute type that indicates an attribute of the update file, a package type that indicates the type of update, and dependency data that indicates condition that must be satisfied by the configuration device 110 or by another medical device 116 so that the update file can be installed on the medical device 114 to be updated. For instance, the dependency data may require the configuration device 110 to be running a most recent version of its respective operating system or may require that a secondary device be updated with a new language file so that the device to be updated can be updated with an update file. The update files are uploaded to the distribution server 102 from an update package source 120 via a portal 106. The update package data can be inputted manually by the update package source using the portal 106.

Figure 2:
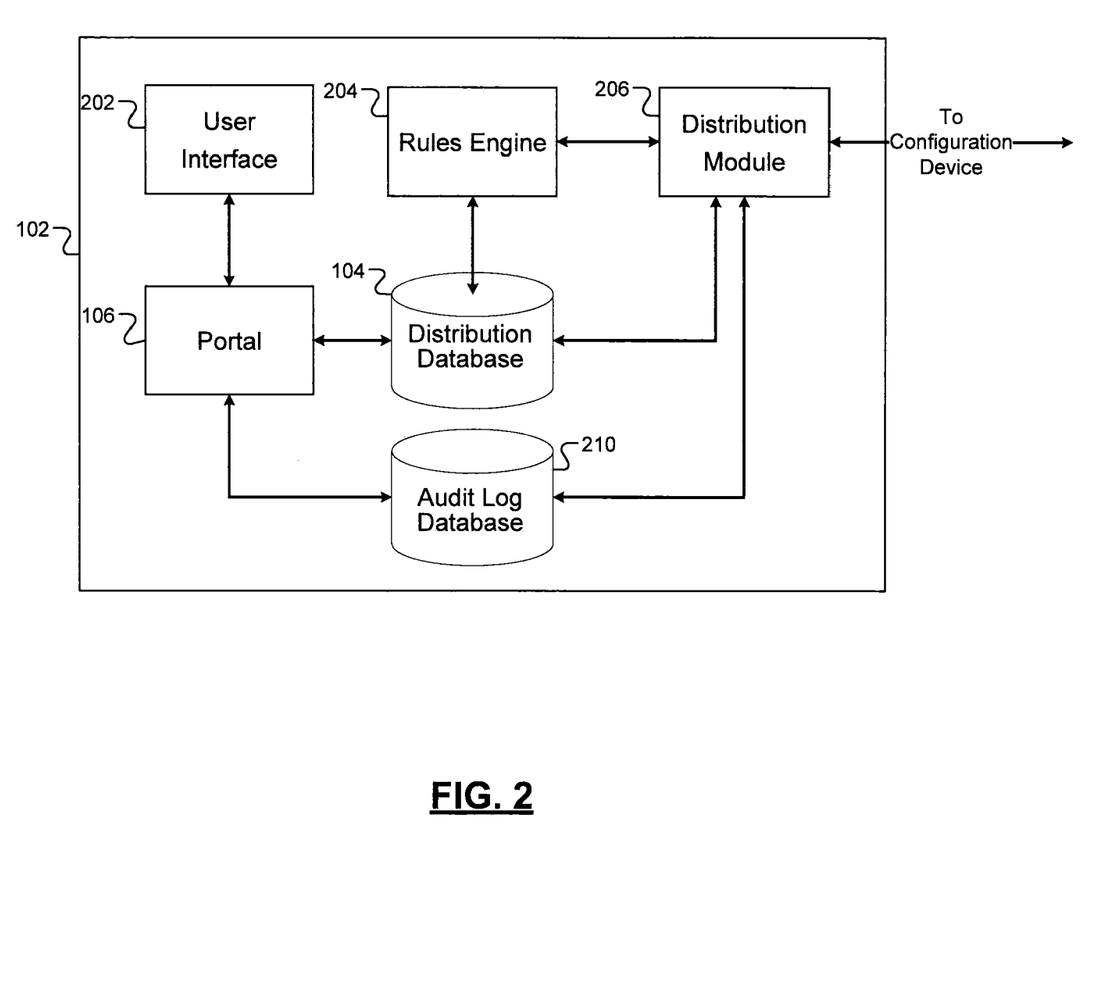
FIG. 2 is a block diagram illustrating exemplary components of a distribution server.

FIG. 2 illustrates exemplary components of the distribution server 102. The distribution server includes the portal 106, the user interface 202, the distribution database 104, a rules engine 204, and a distribution module 206. The user interface 202 provides an interface for update providers to interact with the portal 106. The user interface 202 will display one or more screens which allow the update provider to provide an update package. The user interface 202 can also display screens that provide statistical information to a user regarding various update packages and the usage thereof.

The portal 106 receives from an update provider an update package in the form of an update file and update package data and generates an entry for storage in the distribution database 104 using the update package data. The update package data can contain dependency data corresponding to the update file. The dependency data is also stored in the update package entry, and is used by the rules engine 204 when generating a list of available updates to a configuration device 110. The portal 106 is further configured to store the update file in a file system that is associated with the distribution database 104, the location of which can be stored in the distribution database 104 as part of the update package entry.

The portal 106 is further configured to allow update providers to remove update packages from the system, thereby removing the update packages from publication. It is commonplace for a new update to have errors which make further distribution of the update problematic. Thus, the portal 106 is configured to allow the update provider to pull back an update by removing the update package from the distribution database 104. When an update provider deletes an update package, the portal 106 will purge the update package from the distribution database 104.

The portal 106 may be further configured to allow update providers to enable and disable update packages. In some instances, an update may be compatible with one set of devices or applications but not compatible with another set of devices or applications. For instance, an update for the firmware of a medical device 114 may be suitable for devices in Europe and North America, but not ready for devices in Japan, Australia, China, or Korea. Thus, the update provider can provide instruction to the portal 106 to enable the update package for Europe and North America. Similarly, the update provider can provide instruction to the portal 106 to disable the update package for Japan, Australia, China, and Korea.

The portal 106 is further configured to allow an update provider to view user and product statistics. As will be discussed, the configuration device 110 provides audit logs to the distributions server that provide information on the medical devices and applications. This information can be aggregated and made available to the update providers, via the user interface 202.

The distribution database 104 stores the update package data including the dependency data of the update file of an update package. Further, for each update package, the distribution database 104 stores a location of the update file, e.g. a URL including a file path. The distribution database 104 stores the dependency data of an update file, such that when a request for a particular update file is received, the dependency data is also returned.

Figure 3:
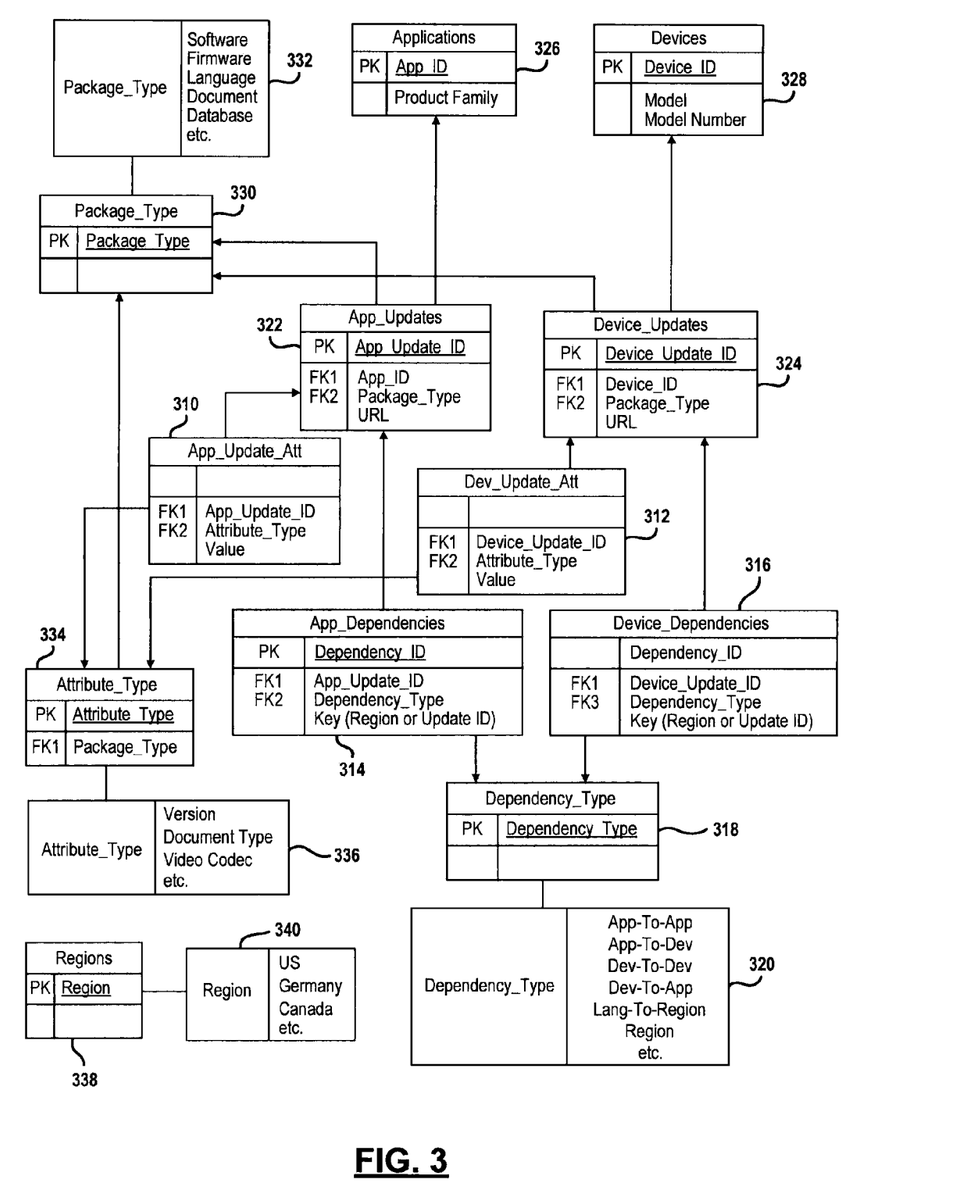
FIG. 3 is a data model illustrating an exemplary structure of a distribution database.

It is appreciated that dependencies can be defined for every update package. As will be discussed, the dependencies are rules that are used by both the distribution module 206 and the rules engine 204 to determine if a device or application can be updated, and what requirements must be satisfied for the update to be performed by the configuration device 110. As mentioned, the distribution database 104 stores the dependencies in relation to corresponding update packages, including device updates and application updates. FIG. 3 illustrates an exemplary data model 300 that shows the structure of a package update entry that can be stored in the distribution database 104. The data model includes an application update attribute element 310 and a device update attribute element 312. The application update attribute element 312 includes foreign keys relating the application update attribute element 312 to an application update element 322 and an attribute type element 334. Similarly, a device update attribute element 312 has foreign keys relating the update attribute element 312 to a device update element 324 and the attribute type element 334. The attribute type 334 stores an attribute type and includes a foreign key that relates the attribute type 334 to a package type element 330. Examples 332 of attribute types include a version, a document type or a video codec.

The data model 300 further includes an application dependency element 314 and a device dependency element 316. The application dependency element 314 has a primary key indicating a dependency identifier for the application, and foreign keys that relate an application dependency element 314 to the application update element 322 and a dependency type element 318. Similarly, the device dependency element 316 includes a primary key indicating a dependency identifier, as well as foreign keys that relate a device dependency element 316 to a device update element 324 and a dependency type element 318. Both the application dependency element 314 and the device dependency element 316 can include a key that references a region element 338 or another update id.

The dependency type element 318 defines a type of dependency. Examples 320 of dependency types include an device-to-device dependency, meaning that an update or action must be performed on a device in order for the update to be performed on a device that is to be updated. It is noted that a device-to-device update can be between a medical device 114 and a configuration device 110, or between a first medical device 114 and one or more other devices 116 and 118. Another example 320 of a dependency type is an application-to-application, meaning that an update or action must be performed on a first application in order for a requested update to be performed on a second application. The dependency types can also include device-to-application, language-to-region, regional dependencies, and other update dependencies.

As mentioned the application update attribute element 310 and the application dependency element 314 both relate to the application update element 322. Similarly, the device update attribute element 312 and the device dependency element 316 both point to the device update element 324. The application update element 322 includes a primary key of an application update identifier and foreign keys that relate an application update element 322 to an application element 326 and to a package type element 330. The application update element 322 can also store a location of an application update file corresponding to the update package, e.g. the URL of the application update file. The device update element 324 includes a primary key indicating a device update identifier and foreign keys that relate a device update element 324 to a device element and the package type element. The device update element 324 can also store a location of a device update file corresponding to the update package.

As mentioned, application update elements 322 relate to an application element 326 and device update elements 324 relate to a device element 328. The application element 326 includes a primary key indicating an application identifier. The application element 326 can further store the product family members of the application, including the products that the application can execute on. The device element 328 includes a primary key that indicates a device identifier and can further store a model and model number of the device.

The package type element 330 is referenced by the application update element 322, the device update element 325 and the attribute type element 334. The package type element 330 includes a package type as a primary key. Examples 332 of package types include a software update, a firmware update, a language update, a document update, and a database update. The region element 338 may be referenced by a dependency element 314 or 316. The region element can include a list of regions that an update is intended for. The regions can be countries, continents, geographical regions, or another geographical division.

The foregoing organization of a distribution database 206 allows the distribution module 206 to provide a device identifier to the distribution database 206 to determine a list of available updates. The distribution database 206 will return device update identifiers of device update elements 324 that relate to device element 328 having the device identifier as a primary key. Further, each device update element 324 can have dependency elements 324 relating thereto. Thus, by providing the device identifier to the distribution database 206, the distribution database can return a list of available updates, and the dependencies for the available updates.

It is appreciated that the foregoing is an exemplary structure of the distribution database 104. It is appreciated that variations of the foregoing are contemplated and within the scope of this disclosure.

Referring back to FIG. 2, the distribution module 206 is an interface between the configuration device 110 and the distribution server 102. The distribution module 206 receives device inquiries from the configuration device 110 on behalf of the medical device 114. A device inquiry can include a firmware version number, a model of the device, a type of device, e.g., a blood glucose meter or a blood pressure meter, a serial number of the device, and/or a region of the device. The distribution module 206 also receives application inquiries from the configuration device 110 on behalf of applications. An application inquiry can include an application version number of the application, a product family of the application, and/or an application identifier that is unique at least to the product family of the application that needs to be updated. The distribution module 206 will receive one or more inquires and will return a list of update packages that contain information regarding the latest versions of device and application updates, including the dependencies of the update packages. The distribution module 206 will also return the locations of the update files of the latest versions of the update packages, such that the configuration device 110 can download the update file from the location.

The distribution module 206 may be further configured to receive audit logs of a device or application from the configuration device 110. An audit log contains records and histories relating to updates performed on a device or application. The information received in the audit logs is stored in the audit log database 208. The audit logs can be used by the portal to display information to a user regarding specific devices, update packages, and versions.

Figure 4:
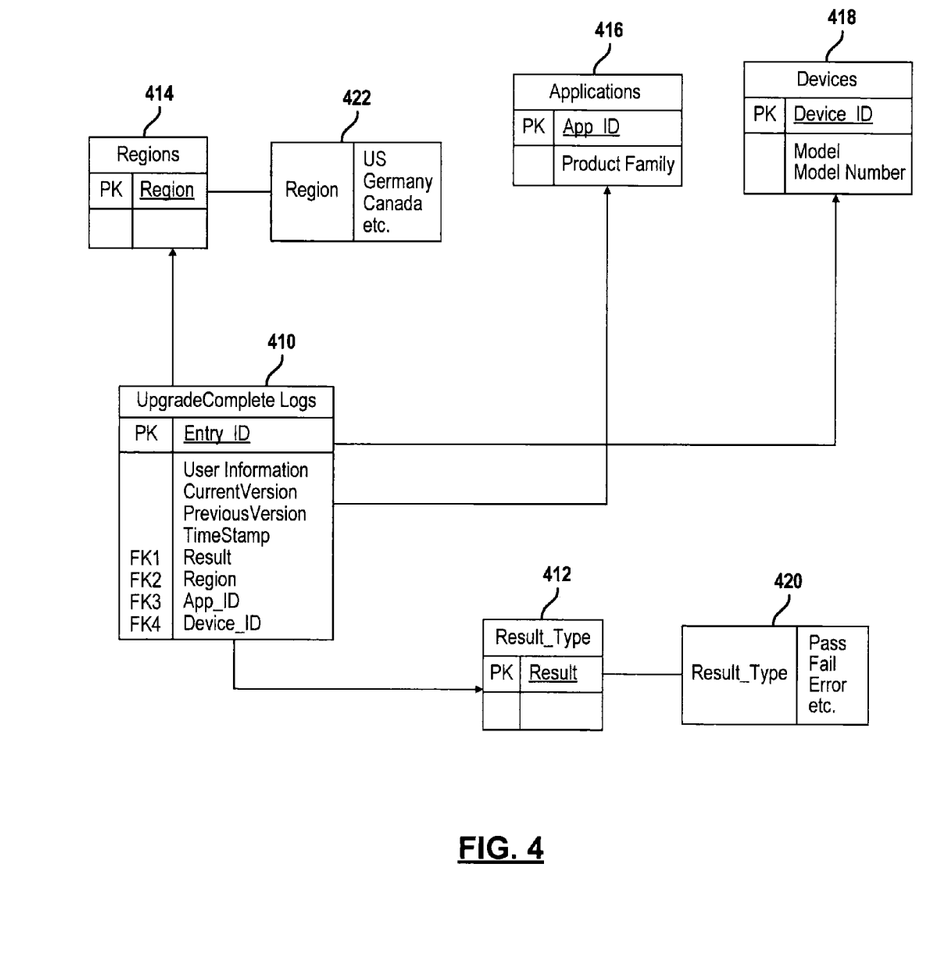
FIG. 4 is a data model illustrating an exemplary structure of an audit log database.

FIG. 4 is a data model illustrating an exemplary structure of the audit log database 208. Each time an audit log is received from a configuration device 210, the distribution module 206 creates an upgrade complete log entry 410. The primary key of the upgrade complete log entry 410 is an entry ID, which is a unique key referencing a previously performed update operation. An upgrade complete log entry 410 can contain user specific information, device specific information, such as the current and previous versions of the update package, and a time stamp. The upgrade complete log entry 410 may further include foreign keys that relate to a result, a region, an application ID, and a device ID. As can be appreciated, each foreign key corresponds to an entry where the foreign key is the primary key. Thus, relating to the upgrade complete log entry 410, there is a result type entry 412, a region entry 414, an application entry 416, and a device entry 418. The results entry 412 stores a result type 420. The result types may include, for example, "pass," "fail," or "error." The regions entry 414 stores a region, such as a country, continent, or geographical region. The application entries have a primary key of an application ID key and may contain the product family of the application. The device entry 418 contains a device ID key. Thus, if a query to the audit log database 208 uses an entry ID, the results would include information contained in the upgrade complete log entry corresponding to the entry ID, as well as the elements for the region entry 414, results 412, application 416 and device entry 418. It is noted that additional elements may be incorporated into the audit log database 208, and that variations of the audit log database 208.

Referring back to FIG. 2, the distribution server 102 may further include a rules engine 204. As discussed, the distribution module 206 will provide a list of available updates to the configuration device 110 and a corresponding list of required updates based on the dependency data. The rules engine 204 queries the distribution database 104 with the device or application information to determine a list of available update packages for the medical device 114 of an application. Further, the rules engine 204 generates the list of required updates based on the list of available updates, the dependency data of the available updates, and a device and/or application information. Although displayed as being a component of the distribution server, it is appreciated that the rules engine 204 may be implemented on the configuration device 110. It is also appreciated that in some embodiments the rules module 206 are implemented on both the distribution server and the configuration device 110, such that the distribution server enforces a subset of rules. In these embodiments, the rules module 206 on the distribution server enforces a subset of the rules or all of the rules, and the rules engine on the configuration device 110 would provide rules for administering off-line updates.

To determine the list of available updates, the rules engine 204 can query the distribution database 104 with information received in an inquiry by the distribution module 206. For instance, the distribution module 206 may receive a device inquiry from the configuration device 110 on behalf of a medical device 114. The device inquiry may indicate a device ID, the current firmware version of the medical device 114, and the region of the device 114. The rules engine 204 can query the distribution device 114 with the type of the device 114 and the region of the device 114. The rules engine 204 will compare the information of the device 114 with the update package entries corresponding to the device ID to determine which, if any, components or files of the device 114 are not current. For instance, if a language file or firmware file of the device 114 are not the most recent versions thereof, the rules engine 204 will determine that the language file or firmware file should be listed as available updates. The rules engine 204 can communicate the available update packages to the distribution module 206, which in turn communicates the list of available update packages to the configuration device 110.

Further, for each available update package, the rules engine 204 analyzes the dependency data of the update package to determine any required updates for the available update package. For example, the medical device 114 may be executing firmware version 3.0 while firmware version 4.0 is the most recent update. In order to install firmware version 4.0, the configuration device 110 must have operating system 2.0, while the configuration device is only running operating system 1.0. In this example, the dependency data of the update package of firmware version 4.0 would be that the configuration device 110 requires version 2.0 in order to perform the update of firmware version 4.0. It is appreciated that the dependency data of an update package can define requirements for the configuration device 110, the medical device 114, and/or other devices 116 and 118. Thus, for each available update package, the rules engine 204 will determine the required update packages for the available update packages, and will provide the required updates to the distribution module 206. For each available update package in the list of available updates, the distribution module 206 will provide the required updates received from the rules engine 204 to the configuration device 110.

It is noted that variations of the distribution module 206 are contemplated. For instance, the distribution module 206 may keep track of a medical device 114 and a corresponding configuration device 110. As new updates become available for the medical device 114, the distribution module 206 can push any new update packages to the configuration device 110, such that when the medical device 114 synchronizes with the configuration device 110, the configuration device 110 is aware of the available updates for the configuration device 110.

Figure 5:
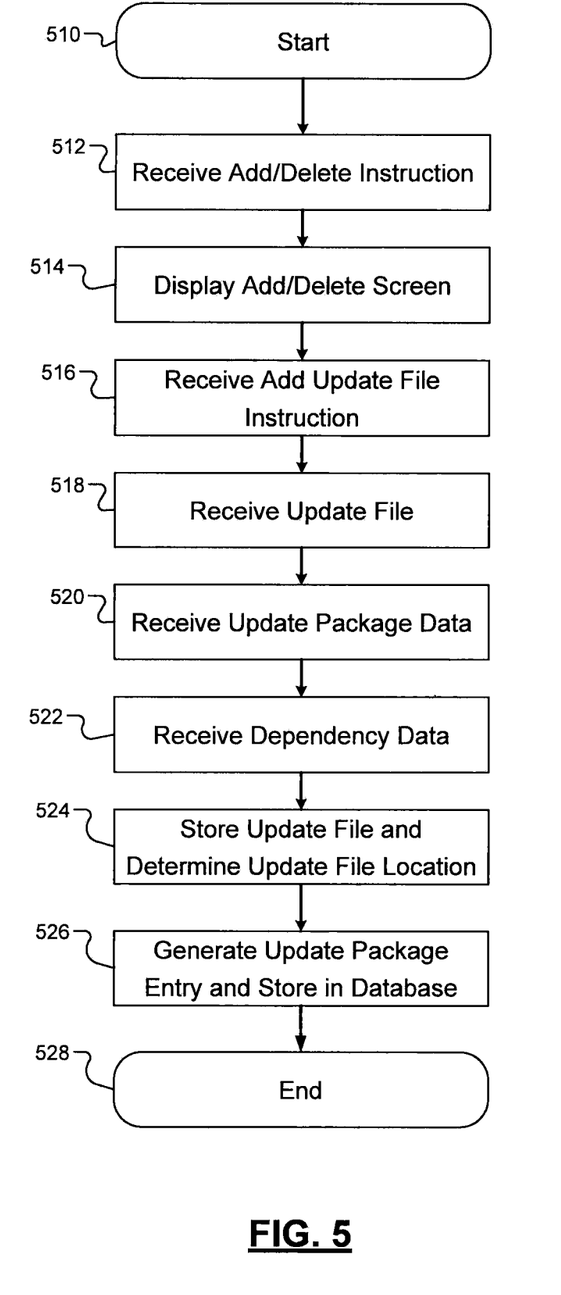
FIG. 5 is a flow chart illustrating an exemplary method for uploading an update package.

As previously discussed, the portal 106 allows update providers to upload update packages to the distribution server 102. The portal 106 receives instructions from a source 120 of the update provider via the user interface 202. Thus, the portal 106 will display different screens to the update provider via the user interface 202. FIG. 5 illustrates an exemplary method that can be executed by the portal 106 to add an update package. The update provider will initially select an Add/Delete function from a home page, which results in an add/delete instruction being sent to the portal, as shown at step 512. Upon receiving such instruction, the portal 106 will display an Add/Delete Packages page to the update provider via the user interface 202, as shown at step 512. The Add/Delete Packages page can include a selectable option to add a package. If the update provider selects the option to add a package, the portal 106 will receive an add update file instruction, as shown at step 516.

Upon receiving the add update file instruction, the portal 106 will prompt the update provider to provide the update file via the user interface 202. The update provider can then upload the update file to the portal, as shown at step 518. For instance the update provider may provide a file path of the update file on the computer of the update provider or a file server associated with the update provider. Upon receiving the update file the portal 106 will prompt the update provider to enter the update package data. The update provider enters the update package data, as shown at step 520. The update package data may include a package type, a version number associated with the package, a material number of the package, a product name associated with the package and a file type associated with the package. The user may further enter languages contained in the package, a country or region that the update package is intended for or any other pertinent data. It is appreciated that the user interface 202 will display a screen or screens with suitable fields, whereby the user is allowed to enter the package data in the fields.

Further, the user will provide the dependency data of the update package to the portal 106, as shown at step 522. The dependency data can be entered in the form of rules indicating conditions that need to be met in order to install the update file. The dependencies can be defined for relationships between the medical device 114 and the configuration device 110, the medical device 114 and another medical device 116, an application of the medical device 114 and the medical device 114, an application of the medical device 114 and the configuration device 110, or other suitable combinations. It is noted that for a particular update package there may be different dependency groups. For instance, the update package may require that the operating system of the configuration device 110 be a particular version number or higher, e.g., 2.0 or higher. Further, another dependency could be that the firmware of the medical device 114 must be version 3.0 or higher. In this example there may be versions 2.0 and 3.0 of the configuration device 110 operation system and there may be versions 3.0, 4.0 and 5.0 of the medical device firmware. The portal 106 defines the dependencies by OR'ing dependencies in a similar group and by AND'ing together the rules of different groups. Thus in the example provided, the dependency data for the update package would be ((configuration device software version 2.0 OR configuration device operation system version 3.0) AND (medical device firmware version 3.0 OR medical device firmware version 4.0 OR medical device firmware version 5.0)).

Once the update package data including the dependency data has been received, the portal 106 stores the update file at a location on the distribution server or a location associated with the distribution server and maintains a file path, as shown at step 524. The portal 106 will then create an update package entry to store and distribute to database 104 based on the received update package data, the dependency data and the location of the update file, as shown at step 526. To generate the update package entry, the portal 106 generates a unique update identification number to associate with the update package, such that the distribution module 206 can reference the update package in future transactions. Once the update package entry is generated and all the relevant fields are filled out, the distribution database 104 is updated.

It is appreciated that the variations of method described above are contemplated and are within the scope of this disclosure. Further, some of the steps described above may be broken up into multiple steps while some steps may be combined into a single step. Further, additional steps may be performed.

The portal 106 is further configured to enable an update package for one or more regions. The portal 106 allows the update provider to select an update package to enable. The update provider selects one or more countries and/or regions for which to enable the update package. Upon receiving the user's selection, the portal 106 will update the update package entry in the distribution database 104 using the newly entered countries and/or regions. Further in some embodiments, the portal 106 may prompt the user to enter an enable date for the country or region. The enable date is a date on which the update package becomes available for download. The portal 106 may confirm that the enable date is equal or subsequent to the current date. The portal 106 can then update the distribution database with the revised update package entry.

The update provider can also disable update packages similarly as described above, the update provider will select an update package and will remove the countries and/or regions for which the update package is being made unavailable to.

In view of the foregoing disclosure, a distribution system for distributing a plurality of update packages to a configuration device has been disclosed. The configuration device is configured to update a plurality of patient medical devices. The distribution system includes a portal that is configured to allow an update package provider to provide a new update package. The new update package includes an update file for a device to be updated and package data corresponding to the update file. The package data includes dependency data indicating a condition that must be satisfied by the configuration device so that the update file of the new update package can be installed on the device to be updated. The distribution system further comprises a database that is configured to store package data of the plurality of update packages and locations of update files of the plurality of update packages including the package data of the new update package and a location of the update file of the new update package. The distribution system further includes a distribution module that is configured to receive an inquiry from the configuration device on behalf of a patient medical device of the plurality of patient medical devices, and to provide a list of update packages including the new update package to the configuration device based on the inquiry and the dependency data of the update packages.

In another aspect of the disclosure, the configuration device is associated with a health care provider and the plurality of patient medical devices are consumer electronics used by medical patients.

In another aspect of the disclosure, the list of update packages indicates available update packages for the patient medical device and required update packages for the configuration device. The update files of the required update packages are required to be installed on the configuration device so that the configuration device can configure the patient medical device with at least one update file of the available update packages.

In another aspect of the disclosure, the system further comprises a rules engine that determines the required update packages based on the available update packages for the patient medical device in the inquiry and the dependency data of the available update packages.

In another aspect of the disclosure, the list of update packages indicates available update packages for an application of the patient medical device and required update packages for the configuration device, wherein update files of the required update packages are required to be installed on the configuration device so that the configuration device can configure the application for the patient medical device with at least one update file of the available update packages.

In another aspect of the disclosure, the patient medical device has geographical region data associated with the patient medical device, such that an inquiry from the configuration device on behalf of the patient medical device includes the geographical region data of the patient medical device.

In another aspect of the disclosure, the dependency data of the plurality of update packages includes geographic location dependency data indicating geographic locations that the update package can be installed in, wherein the list of update packages provided to the configuration device indicates available update packages for the patient medical device and the available update packages are based on the geographic location data of patient medical device indicated in the inquiry and the geographic location dependency data of the available update packages.

In another aspect of the disclosure, the portal is configured to receive an instruction to enable a previously stored update package for patient medical devices in a particular geographic location and to modify geographic location dependency data of the previously stored update package based on the received instruction.

In another aspect of the disclosure, the portal is configured to receive the update file and the package data and to generate a corresponding update package for storage in the database.

In another aspect of the disclosure, the update package data indicates whether the update file is intended for a patient medical device or an application.

In another aspect of the disclosure, the portal allows the update package provider to upload the update file from a device associated with the update package provider and to enter the package data via a user interface.

In another aspect of the disclosure, a distribution system for distributing a plurality of update packages to a configuration device is disclosed. The configuration device is configured to update a plurality of patient medical devices. The system comprises a portal that is configured to allow an update package provider to provide a new update package. The new update package includes an update file for a patient medical device to be updated and package data corresponding to the update file. The package data includes dependency data indicating a condition that must be satisfied by a different patient medical device so that the update file of the new update package can be installed on the patient medical device to be updated. The system further comprises a database that is configured to store package data of the plurality of update packages and locations of update files of the plurality of update packages including the package data of the new update package and a location of the update file of the new update package. The system also includes a distribution module that is configured to receive an inquiry from the configuration device on behalf of a first patient medical device of the plurality of patient medical devices, and to provide a list of update packages including the new update package to the configuration device based on the inquiry and the dependency data of the update packages.

In another aspect of the disclosure, the configuration device is associated with a health care provider and the plurality of patient medical devices are associated with medical patients.

In another aspect of the disclosure, the list of update packages indicates available update packages for the first patient medical device and required update packages for a second patient medical device. The update files of the required update packages are required to be installed on the second patient medical device so that the configuration device can configure the first patient medical device with at least one update file of the available update packages.

In another aspect of the disclosure, the system further comprises a rules engine that determines the required update packages for the second patient medical device based on the available update packages for the first patient medical device in the inquiry and the dependency data of the available update packages.

In another aspect of the disclosure, the list of update packages indicates available update packages for an application of the first patient medical device and required update packages for the second patient medical device. The update files of the required update packages are required to be installed on the second patient medical device, so that the configuration device can configure the application for the first patient medical device with an update file of the available update packages.

In another aspect of the disclosure, the first patient medical device has geographical region data associated with the patient medical device, such that an inquiry from the configuration device on behalf of the first patient medical device includes the geographical region data of the patient medical device. The dependency data of the plurality of update packages includes geographic location dependency data indicating geographic locations that the update package can be installed in. The list of update packages provided to the configuration device indicates available update packages for the patient medical device and the available update packages are based on the geographic location data of patient medical device indicated in the inquiry and the geographic location dependency data of the available update packages.

In another aspect of the disclosure, the portal is configured to receive an instruction to enable a previously stored update package for patient medical devices associated to a particular geographic location and to modify geographic location dependency data of the previously stored update package based on the received instruction.

In another aspect of the disclosure, the portal is configured to receive the update file and the package data and to generate a corresponding update package for storage in the database.

In another aspect of the disclosure, the portal allows the update package provider to upload the update file from a device associated with the update package provider and to enter the package data via a user interface.

What is claimed is:
1. A distribution system comprising:
a plurality of processors coupled to memory, executing instructions configured to distribute a plurality of update packages to a configuration device, the configuration device being configured to update a plurality of patient medical devices;

a portal that is configured to allow an update provider to provide a new update package, wherein the new update package includes an update file for a patient medical device to be updated and package data corresponding to the update file, the package data including dependency data indicating a condition that must be satisfied by the configuration device so that the update file of the new update package can be installed on the patient medical device to be updated, wherein the patient medical device has geographical region data associated with the patient medical device, such that an inquiry from the configuration device on behalf of the patient medical device includes the geographical region data of the patient medical device, wherein the dependency data of the plurality of update packages includes geographic location dependency data indicating geographic locations that the update package can be installed in, wherein the list of update packages provided to the configuration device indicates available update packages for the patient medical device and the available update packages are based on the geographic location data of patient medical device indicated in the inquiry and the geographic location dependency data of the available update packages;

a database that is configured to store package data of the plurality of update packages and locations of update files of the plurality of update packages including the package data of the new update package and a location of the update file of the new update package;

a distribution server that is configured to receive the inquiry from the configuration device on behalf of a first patient medical device of the plurality of patient medical devices, and to provide a list of update packages including the new update package to the configuration device based on the inquiry and the dependency data of the update packages, wherein the list of update packages indicates available update packages for the first patient medical device and required update packages for a second patient medical device that has dependencies with the first medical device, wherein update files of the required update packages are required to be installed on the second patient medical device so that the configuration device can configure the first patient medical device with at least one update file of the available update packages.

2. The system of claim 1 wherein the configuration device is associated with a health care provider and the plurality of patient medical devices are consumer electronics used by medical patients.

3. The system of claim 1 wherein the list of update packages indicates available update packages for the patient medical device and required update packages for the configuration device, wherein update files of the required update packages are required to be installed on the configuration device so that the configuration device can configure the patient medical device with at least one update file of the available update packages.

4. The system of claim 3 further comprising a rules engine that determines the required update packages based on the available update packages for the patient medical device in the inquiry and the dependency data of the available update packages.

5. The system of claim 1 wherein the list of update packages indicates available update packages for an application of the patient medical device and required update packages for the configuration device, wherein update files of the required update packages are required to be installed on the configuration device so that the configuration device can configure the application for the patient medical device with at least one update file of the available update packages.

6. The system of claim 1 wherein the portal is configured to receive an instruction to enable a previously stored update package for patient medical devices in a particular geographic location and to modify geographic location dependency data of the previously stored update package based on the received instruction.

7. The system of claim 1 wherein the portal is configured to receive the update file and the package data and to generate a corresponding update package for storage in the database.

8. The system of claim 7 wherein the update package data indicates whether the update file is intended for a patient medical device or an application.

9. The system of claim 7 wherein the portal allows the update package provider to upload the update file from a device associated with the update package provider and to enter the package data via a user interface.

* * * * *